(12) United States Patent
Machida et al.

(10) Patent No.: US 7,285,407 B2
(45) Date of Patent: Oct. 23, 2007

(54) GENES OF CELL WALL-DEGRADING ENZYMES DERIVED FROM ASPERGILLUS, AND METHOD FOR THE PRODUCTION THE ENZYMES

(75) Inventors: Masayuki Machida, Tsukuba (JP); Motoaki Sano, Tsukuba (JP); Misao Sunagawa, Tsukuba (JP); Tasuku Nakajima, Sendai (JP); Keietsu Abe, Sendai (JP); Katsuya Gomi, Sendai (JP); Kiyoshi Asai, Tokyo (JP); Taishin Kin, Tokyo (JP); Hideki Nagasaki, Tokyo (JP); Akira Hosoyama, Tokyo (JP); Osamu Akita, Hiroshima (JP); Naotake Ogasawara, Nara (JP); Satoru Kuhara, Fukuoka (JP)

(73) Assignees: National Institute of Advanced Industrial Science and Technology, Tokyo (JP); National Institute of Technology and Evaluation, Tokyo (JP)

( * ) Notice: Subject to any disclaimer, the term of this patent is extended or adjusted under 35 U.S.C. 154(b) by 0 days.

(21) Appl. No.: 11/085,185

(22) Filed: Mar. 22, 2005

(65) Prior Publication Data

US 2005/0287634 A1 Dec. 29, 2005

(30) Foreign Application Priority Data

Jun. 25, 2004 (JP) .............................. 2004-188849

(51) Int. Cl.
| | |
|---|---|
| *C12N 9/24* | (2006.01) |
| *C12N 9/30* | (2006.01) |
| *C12N 1/00* | (2006.01) |
| *C12N 15/00* | (2006.01) |
| *C12P 21/06* | (2006.01) |
| *C07H 21/02* | (2006.01) |
| *C07H 21/04* | (2006.01) |

(52) U.S. Cl. ............... 435/200; 435/203; 435/69.1; 435/254.1; 435/254.11; 435/254.3; 435/320.1; 435/252.3; 536/23.1; 536/23.2; 536/23.74

(58) Field of Classification Search ............. 435/320.1, 435/68.1, 252.3, 254.11, 183
See application file for complete search history.

(56) References Cited

U.S. PATENT DOCUMENTS

2003/0119013 A1* 6/2003 Jiang et al. ..................... 435/6

FOREIGN PATENT DOCUMENTS

WO    WO02086090 A2    10/2002

OTHER PUBLICATIONS

Mouyna et al., Molecular characterization of a cell wall-associated beta (1-3)endoglucnase of *Aspergillus fumigatus*. Medical Mycology, 2002, vol. 40 (5); 455-464. (Abstract only. Full length article has been ordered).*
Niblett et al., UNIPROT: Q09850, Accession No. S62501, 1995.

* cited by examiner

*Primary Examiner*—Rebecca E. Prouty
*Assistant Examiner*—Ganapathirama Raghu
(74) *Attorney, Agent, or Firm*—Birch, Stewart, Kolasch & Birch, LLP

(57) ABSTRACT

The purpose of the present invention is to isolate a gene encoding novel exo-, or endo-β-1,3-glucanase, to obtain a microorganism having an enhanced expression of said gene and to degrade β-1,3-glucan to its low molecular weight form by means of said enzymes. The present invention relates to a gene or DNA encoding novel enzymes having β-1,3-glucanase activity (exo-, or endo-β-1,3-glucanase), a recombinant expression vector comprising them, a microorganism having the recombinant expression vector, the novel enzymes having β-1,3-glucanase activity, and a method for the production of said enzymes.

7 Claims, 4 Drawing Sheets

Figure 1:
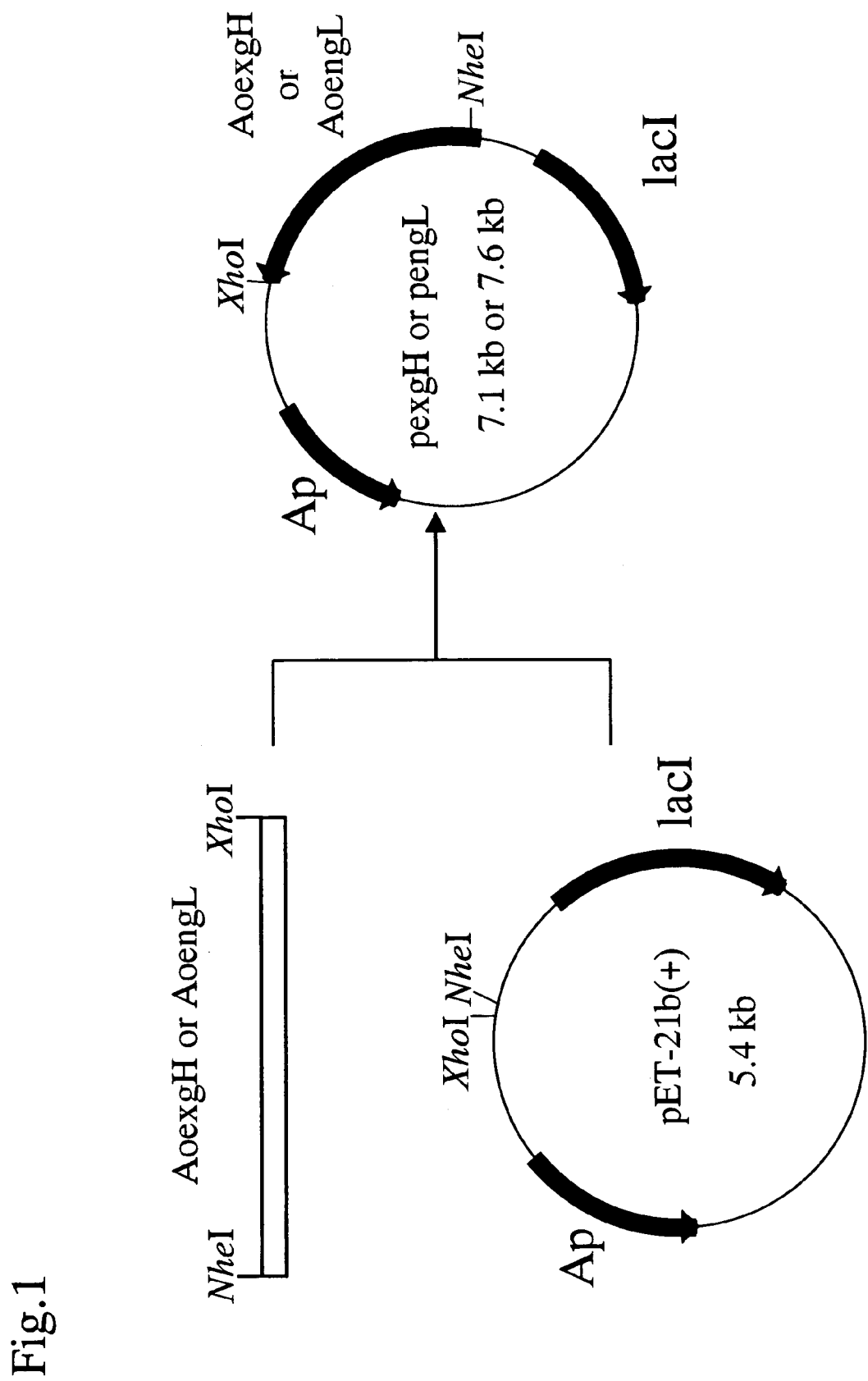

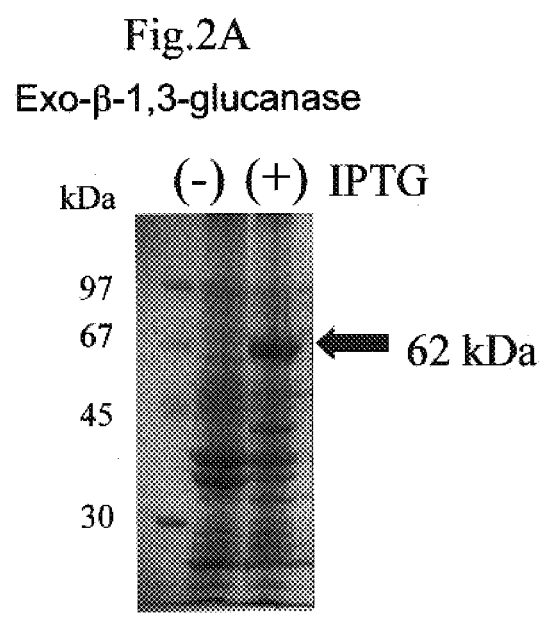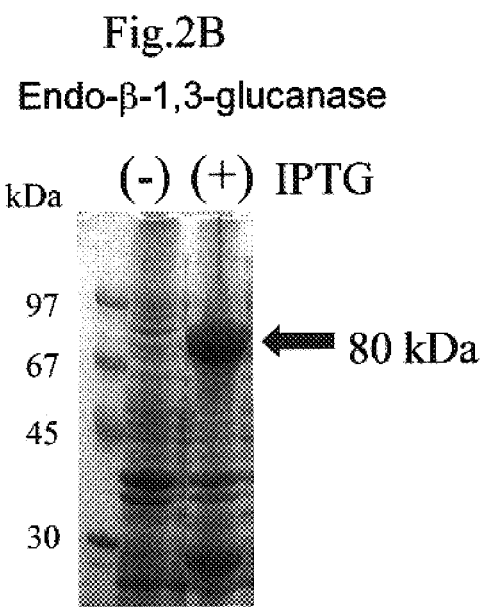
Fig.2A
Exo-β-1,3-glucanase
Fig.2B
Endo-β-1,3-glucanase

SEQUENCE LISTING

<160> NUMBER OF SEQ ID NOS: 14

<210> SEQ ID NO 1
<211> LENGTH: 1650
<212> TYPE: DNA
<213> ORGANISM: Aspergillus oryzae
<220> FEATURE:
<221> NAME/KEY: CDS

<222> LOCATION: (1)..(1650)

<400> SEQUENCE: 1

```
atg gag ggc tcc gat gca caa ccg ccg ttc tgg aag cgg aag aaa tgg      48
Met Glu Gly Ser Asp Ala Gln Pro Pro Phe Trp Lys Arg Lys Lys Trp
1               5                   10                  15 tgg att gtc ata ggg gtg ctg gtc gtc gtt ctc gct att gtt atc cca      96
Trp Ile Val Ile Gly Val Leu Val Val Val Leu Ala Ile Val Ile Pro
            20                  25                  30 gtt gct gtc gtt atg tct aag aaa cat ggt cat gat gat gat aaa tca     144
Val Ala Val Val Met Ser Lys Lys His Gly His Asp Asp Asp Lys Ser
        35                  40                  45 ggc tca agc tct tcc gtc gat aac agc gac tcg cct tac atc tca agt     192
Gly Ser Ser Ser Ser Val Asp Asn Ser Asp Ser Pro Tyr Ile Ser Ser
    50                  55                  60 ttg gat ggg cta agt cac gat agc att cca gaa tct gct cag ggg tca     240
Leu Asp Gly Leu Ser His Asp Ser Ile Pro Glu Ser Ala Gln Gly Ser
65                  70                  75                  80 ata ctg gat ccc tgg acg tgg tac gac acg aga gac ttt aac ctg acc     288
Ile Leu Asp Pro Trp Thr Trp Tyr Asp Thr Arg Asp Phe Asn Leu Thr
                85                  90                  95 ttt acc aac gag acg gtc ggt ggc ctt ccc atc atg ggg cta aac tca     336
Phe Thr Asn Glu Thr Val Gly Gly Leu Pro Ile Met Gly Leu Asn Ser
            100                 105                 110 aca tgg gat gac tca aca agg ccc aac gac aat gtg ccc cca ttg aac     384
Thr Trp Asp Asp Ser Thr Arg Pro Asn Asp Asn Val Pro Pro Leu Asn
        115                 120                 125 gaa tcc ttc ccg tac ggt tcg caa ccg att cgc ggt gtg aat ctt ggg     432
Glu Ser Phe Pro Tyr Gly Ser Gln Pro Ile Arg Gly Val Asn Leu Gly
    130                 135                 140 ggg tgg ctg tca atc gag ccc ttt att gtc cct tca tta ttc gag aat     480
Gly Trp Leu Ser Ile Glu Pro Phe Ile Val Pro Ser Leu Phe Glu Asn
145                 150                 155                 160 tac tca agc aag gac aga att atc gac gag tat aca ttg tgc aaa aag     528
Tyr Ser Ser Lys Asp Arg Ile Ile Asp Glu Tyr Thr Leu Cys Lys Lys
                165                 170                 175 ctc gga tcg tcc gct gcc tca acg atc gaa aag cat tat gca gac ttt     576
Leu Gly Ser Ser Ala Ala Ser Thr Ile Glu Lys His Tyr Ala Asp Phe
            180                 185                 190 atc tca gaa caa gat ttt ata gac atg agg gat gca gga ctg gat cat     624
Ile Ser Glu Gln Asp Phe Ile Asp Met Arg Asp Ala Gly Leu Asp His
        195                 200                 205 gtt cgc atc cag ttc tcc tac tgg gcg gtg acg acg tac gac gat gat     672
Val Arg Ile Gln Phe Ser Tyr Trp Ala Val Thr Thr Tyr Asp Asp Asp
    210                 215                 220 ccg tat gtc gca aaa atc tca tgg agg tac ctc ttg cga gcc att gaa     720
Pro Tyr Val Ala Lys Ile Ser Trp Arg Tyr Leu Leu Arg Ala Ile Glu
225                 230                 235                 240 tac tgc cga aag tac ggg ctt cgc gta aac ttg gat ccc cat ggc atc     768
Tyr Cys Arg Lys Tyr Gly Leu Arg Val Asn Leu Asp Pro His Gly Ile
                245                 250                 255 ccg ggt agc caa aat ggc tgg aac cac agc ggc cgc gag gga gtc atc     816
Pro Gly Ser Gln Asn Gly Trp Asn His Ser Gly Arg Glu Gly Val Ile
            260                 265                 270 ggc tgg ttg aat ggt aca gat ggc caa ctt aac aga cag cgc tct ctc     864
Gly Trp Leu Asn Gly Thr Asp Gly Gln Leu Asn Arg Gln Arg Ser Leu
        275                 280                 285 gac ttc cac aac caa atc tcg cag ttc ttt gca caa ccc cgc tac aag     912
Asp Phe His Asn Gln Ile Ser Gln Phe Phe Ala Gln Pro Arg Tyr Lys
    290                 295                 300
```

```
aat gtt gtt aca atc tac ggc ctc gtc aat gaa cca ctc atg ctc tca      960
Asn Val Val Thr Ile Tyr Gly Leu Val Asn Glu Pro Leu Met Leu Ser
305                 310                 315                 320 ttg ccg gtt gag gac gta tta aat tgg acg aca gat gcc acg aaa cta     1008
Leu Pro Val Glu Asp Val Leu Asn Trp Thr Thr Asp Ala Thr Lys Leu
                325                 330                 335 gtg cag aag aac ggt att tca gcc tat gtc acc gtc cac gac ggc ttc     1056
Val Gln Lys Asn Gly Ile Ser Ala Tyr Val Thr Val His Asp Gly Phe
            340                 345                 350 ttg aac ttg agt aaa tgg aag caa atg ctg aag gac cgg ccg gac cgg     1104
Leu Asn Leu Ser Lys Trp Lys Gln Met Leu Lys Asp Arg Pro Asp Arg
        355                 360                 365 atg ttt ctt gac act cac cag tac acc atc ttc aac acg gga caa att     1152
Met Phe Leu Asp Thr His Gln Tyr Thr Ile Phe Asn Thr Gly Gln Ile
370                 375                 380 gtc ctt aat cac acg gac cga gtg aag ctc atc tgt aat gac tgg tac     1200
Val Leu Asn His Thr Asp Arg Val Lys Leu Ile Cys Asn Asp Trp Tyr
385                 390                 395                 400 aac atg atc aaa gag atc aac acc aca agt gca ggc tgg ggc cca acc     1248
Asn Met Ile Lys Glu Ile Asn Thr Thr Ser Ala Gly Trp Gly Pro Thr
                405                 410                 415 atc tgc ggc gaa tgg tcc caa gct gat acc gac tgt gcc caa tac ctc     1296
Ile Cys Gly Glu Trp Ser Gln Ala Asp Thr Asp Cys Ala Gln Tyr Leu
            420                 425                 430 aac aac gtc ggc cgc ggc acc cgc tgg gaa ggc acc ttt gct ata ggc     1344
Asn Asn Val Gly Arg Gly Thr Arg Trp Glu Gly Thr Phe Ala Ile Gly
        435                 440                 445 gac tca aca gtt tat tgt ccc acc gct gac aca ggt cca acc tgt agc     1392
Asp Ser Thr Val Tyr Cys Pro Thr Ala Asp Thr Gly Pro Thr Cys Ser
450                 455                 460 tgt gcc tcc gcc aat gcc cct ccc gcc gat tac tca gac ggt tac aag     1440
Cys Ala Ser Ala Asn Ala Pro Pro Ala Asp Tyr Ser Asp Gly Tyr Lys
465                 470                 475                 480 aaa ttc ctt caa aca tat gcc gaa gcg caa atg tct gca ttt gga aca     1488
Lys Phe Leu Gln Thr Tyr Ala Glu Ala Gln Met Ser Ala Phe Gly Thr
                485                 490                 495 gcc cag ggc tgg ttt tat tgg acg tgg cat acc gag tcc gct gcc cag     1536
Ala Gln Gly Trp Phe Tyr Trp Thr Trp His Thr Glu Ser Ala Ala Gln
            500                 505                 510 tgg agc tat aaa aca gct tgg aag aat ggc tat atg cca aag aaa gct     1584
Trp Ser Tyr Lys Thr Ala Trp Lys Asn Gly Tyr Met Pro Lys Lys Ala
        515                 520                 525 tac gct ccc gat ttc aag tgc ggt gat gat att ccg agt ttc ggg gat     1632
Tyr Ala Pro Asp Phe Lys Cys Gly Asp Asp Ile Pro Ser Phe Gly Asp
530                 535                 540 tta ccg gaa tat tat taa                                             1650
Leu Pro Glu Tyr Tyr
545

<210> SEQ ID NO 2
<211> LENGTH: 549
<212> TYPE: PRT
<213> ORGANISM: Aspergillus oryzae

<400> SEQUENCE: 2

Met Glu Gly Ser Asp Ala Gln Pro Pro Phe Trp Lys Arg Lys Lys Trp
1               5                   10                  15

Trp Ile Val Ile Gly Val Leu Val Val Val Leu Ala Ile Val Ile Pro
                20                  25                  30
```

-continued

```
Val Ala Val Met Ser Lys Lys His Gly His Asp Asp Lys Ser
         35              40              45

Gly Ser Ser Ser Ser Val Asp Asn Ser Asp Ser Pro Tyr Ile Ser Ser
         50              55              60

Leu Asp Gly Leu Ser His Asp Ser Ile Pro Glu Ser Ala Gln Gly Ser
65              70              75              80

Ile Leu Asp Pro Trp Thr Trp Tyr Asp Thr Arg Asp Phe Asn Leu Thr
             85              90              95

Phe Thr Asn Glu Thr Val Gly Gly Leu Pro Ile Met Gly Leu Asn Ser
             100             105             110

Thr Trp Asp Asp Ser Thr Arg Pro Asn Asp Asn Val Pro Pro Leu Asn
             115             120             125

Glu Ser Phe Pro Tyr Gly Ser Gln Pro Ile Arg Gly Val Asn Leu Gly
     130             135             140

Gly Trp Leu Ser Ile Glu Pro Phe Ile Val Pro Ser Leu Phe Glu Asn
145             150             155             160

Tyr Ser Ser Lys Asp Arg Ile Ile Asp Glu Tyr Thr Leu Cys Lys Lys
                 165             170             175

Leu Gly Ser Ser Ala Ala Ser Thr Ile Glu Lys His Tyr Ala Asp Phe
             180             185             190

Ile Ser Glu Gln Asp Phe Ile Asp Met Arg Asp Ala Gly Leu Asp His
             195             200             205

Val Arg Ile Gln Phe Ser Tyr Trp Ala Val Thr Thr Tyr Asp Asp Asp
     210             215             220

Pro Tyr Val Ala Lys Ile Ser Trp Arg Tyr Leu Leu Arg Ala Ile Glu
225             230             235             240

Tyr Cys Arg Lys Tyr Gly Leu Arg Val Asn Leu Asp Pro His Gly Ile
                 245             250             255

Pro Gly Ser Gln Asn Gly Trp Asn His Ser Gly Arg Glu Gly Val Ile
             260             265             270

Gly Trp Leu Asn Gly Thr Asp Gly Gln Leu Asn Arg Gln Arg Ser Leu
     275             280             285

Asp Phe His Asn Gln Ile Ser Gln Phe Phe Ala Gln Pro Arg Tyr Lys
     290             295             300

Asn Val Val Thr Ile Tyr Gly Leu Val Asn Glu Pro Leu Met Leu Ser
305             310             315             320

Leu Pro Val Glu Asp Val Leu Asn Trp Thr Thr Asp Ala Thr Lys Leu
             325             330             335

Val Gln Lys Asn Gly Ile Ser Ala Tyr Val Thr Val His Asp Gly Phe
             340             345             350

Leu Asn Leu Ser Lys Trp Lys Gln Met Leu Lys Asp Arg Pro Asp Arg
             355             360             365

Met Phe Leu Asp Thr His Gln Tyr Thr Ile Phe Asn Thr Gly Gln Ile
     370             375             380

Val Leu Asn His Thr Asp Arg Val Lys Leu Ile Cys Asn Asp Trp Tyr
385             390             395             400

Asn Met Ile Lys Glu Ile Asn Thr Thr Ser Ala Gly Trp Gly Pro Thr
             405             410             415

Ile Cys Gly Glu Trp Ser Gln Ala Asp Thr Asp Cys Ala Gln Tyr Leu
             420             425             430

Asn Asn Val Gly Arg Gly Thr Arg Trp Glu Gly Thr Phe Ala Ile Gly
             435             440             445

Asp Ser Thr Val Tyr Cys Pro Thr Ala Asp Thr Gly Pro Thr Cys Ser
```

```
                450              455              460
Cys Ala Ser Ala Asn Ala Pro Pro Ala Asp Tyr Ser Asp Gly Tyr Lys
465                 470                  475                  480

Lys Phe Leu Gln Thr Tyr Ala Glu Ala Gln Met Ser Ala Phe Gly Thr
                485                 490                  495

Ala Gln Gly Trp Phe Tyr Trp Thr Trp His Thr Glu Ser Ala Ala Gln
            500                 505                  510

Trp Ser Tyr Lys Thr Ala Trp Lys Asn Gly Tyr Met Pro Lys Lys Ala
        515                 520                  525

Tyr Ala Pro Asp Phe Lys Cys Gly Asp Asp Ile Pro Ser Phe Gly Asp
530                 535                  540

Leu Pro Glu Tyr Tyr
545

<210> SEQ ID NO 3
<211> LENGTH: 2211
<212> TYPE: DNA
<213> ORGANISM: Aspergillus oryzae
<220> FEATURE:
<221> NAME/KEY: CDS
<222> LOCATION: (1)..(2211)

<400> SEQUENCE: 3 atg gcg aca atg gca aac ggt caa gat gtg ttt ctg cca gta tct acc      48
Met Ala Thr Met Ala Asn Gly Gln Asp Val Phe Leu Pro Val Ser Thr
1               5                   10                  15 ggc cca att ccc gga aca gtg aag tca cgg aat gac cac cca gtc ccc      96
Gly Pro Ile Pro Gly Thr Val Lys Ser Arg Asn Asp His Pro Val Pro
            20                  25                  30 agg gcc tcc ata atg aac aac acg gac ccg att gaa aca aac aag ttc     144
Arg Ala Ser Ile Met Asn Asn Thr Asp Pro Ile Glu Thr Asn Lys Phe
        35                  40                  45 tac gcc gga ttg ttc cta ggg act caa acc aat aca acc ttc aca cat     192
Tyr Ala Gly Leu Phe Leu Gly Thr Gln Thr Asn Thr Thr Phe Thr His
50                  55                  60 cca tat ggg att gcg tgg gca aag ggg aac ggg aat gcg aaa agc tac     240
Pro Tyr Gly Ile Ala Trp Ala Lys Gly Asn Gly Asn Ala Lys Ser Tyr
65                  70                  75                  80 ggc atg gct atc tcg cat att gag gca gac aag ctt gct ttg ggg ccg     288
Gly Met Ala Ile Ser His Ile Glu Ala Asp Lys Leu Ala Leu Gly Pro
                85                  90                  95 aaa aat gac aag ata cca ggc agc cca gtt caa tat tac gtg aac cct     336
Lys Asn Asp Lys Ile Pro Gly Ser Pro Val Gln Tyr Tyr Val Asn Pro
            100                 105                 110 att ggt atc cag tcc att ata tta tcg gca act gaa ttg ggg ggc tct     384
Ile Gly Ile Gln Ser Ile Ile Leu Ser Ala Thr Glu Leu Gly Gly Ser
        115                 120                 125 act gtg ctt atg aca gag aat ccg ctg cca ttc tcg gcg aac gct gtc     432
Thr Val Leu Met Thr Glu Asn Pro Leu Pro Phe Ser Ala Asn Ala Val
130                 135                 140 ttg caa cct cag agt gga tca tct gag agg atc acc ttt ccc gta gta     480
Leu Gln Pro Gln Ser Gly Ser Ser Glu Arg Ile Thr Phe Pro Val Val
145                 150                 155                 160 cag ggc atg ggt ttt gtc acc ggg ata tat tcg aac ctt cag ccc gtt     528
Gln Gly Met Gly Phe Val Thr Gly Ile Tyr Ser Asn Leu Gln Pro Val
                165                 170                 175 att cag agc agt gtt ttc ttc agc aaa gta gtc tct gct ggt tct cca     576
Ile Gln Ser Ser Val Phe Phe Ser Lys Val Val Ser Ala Gly Ser Pro
            180                 185                 190
```

-continued

| | |
|---|---|
| aga cct ggt att ttc aaa tat acc gtg gat ctt gca gat ggg acc aat<br>Arg Pro Gly Ile Phe Lys Tyr Thr Val Asp Leu Ala Asp Gly Thr Asn<br>    195                    200                    205 | 624 |
| tgg ctt ctt tac cta act tca aat gat ggg aaa gat cca aat ctc cat<br>Trp Leu Leu Tyr Leu Thr Ser Asn Asp Gly Lys Asp Pro Asn Leu His<br>210                    215                    220 | 672 |
| ctg gag tcc act acc aac ctg cgt ggg cct cct ggc tgg tca gga aca<br>Leu Glu Ser Thr Thr Asn Leu Arg Gly Pro Pro Gly Trp Ser Gly Thr<br>225                    230                    235                    240 | 720 |
| gtg cag gtg gcc aaa aac cca gca ggt aca ttg gga gag aaa cta ttc<br>Val Gln Val Ala Lys Asn Pro Ala Gly Thr Leu Gly Glu Lys Leu Phe<br>                    245                    250                    255 | 768 |
| gac aat tcg tct ggt gtc tat gcc aca caa ggt tgg gtg aaa ggt gct<br>Asp Asn Ser Ser Gly Val Tyr Ala Thr Gln Gly Trp Val Lys Gly Ala<br>              260                    265                    270 | 816 |
| gta tct ggt cag acg gga aca tac agc ctc acg tgg ggg aag gag ggc<br>Val Ser Gly Gln Thr Gly Thr Tyr Ser Leu Thr Trp Gly Lys Glu Gly<br>            275                    280                    285 | 864 |
| aaa gat aaa gac ggt acc cca ttg atg atg tat gct ctg ccg cac cac<br>Lys Asp Lys Asp Gly Thr Pro Leu Met Met Tyr Ala Leu Pro His His<br>290                    295                    300 | 912 |
| gtg gaa tca ttt gat aaa act acc cac gac cgc ctg aca aat atc acg<br>Val Glu Ser Phe Asp Lys Thr Thr His Asp Arg Leu Thr Asn Ile Thr<br>305                    310                    315                    320 | 960 |
| atg cgc aca acc aca aag ggc aat gca aca gca gtc atc ggg gag act<br>Met Arg Thr Thr Thr Lys Gly Asn Ala Thr Ala Val Ile Gly Glu Thr<br>                    325                    330                    335 | 1008 |
| tgg tca atg gtg gaa cag gat ctg cct gtt ggt atg gga ttt gcc ccg<br>Trp Ser Met Val Glu Gln Asp Leu Pro Val Gly Met Gly Phe Ala Pro<br>              340                    345                    350 | 1056 |
| tgg tct gtg tcc gca ggc agc gtc gac acg att tct ccg gcg gcc caa<br>Trp Ser Val Ser Ala Gly Ser Val Asp Thr Ile Ser Pro Ala Ala Gln<br>            355                    360                    365 | 1104 |
| aaa gtc atc ata gat gtg gca cca aca gag ctg caa cag gac gtc ggc<br>Lys Val Ile Ile Asp Val Ala Pro Thr Glu Leu Gln Gln Asp Val Gly<br>370                    375                    380 | 1152 |
| aat caa tcc aac ttg aat agc atg tat tac agc ggc aaa gct ctc agc<br>Asn Gln Ser Asn Leu Asn Ser Met Tyr Tyr Ser Gly Lys Ala Leu Ser<br>385                    390                    395                    400 | 1200 |
| aaa ttc gct acg ctc gta tac gcc gtg gac aaa ttg ggt ggc aag ccc<br>Lys Phe Ala Thr Leu Val Tyr Ala Val Asp Lys Leu Gly Gly Lys Pro<br>                    405                    410                    415 | 1248 |
| gac ctt gca gcc cct gct ctg aag gac cta aag acg gcc ttc gct cga<br>Asp Leu Ala Ala Pro Ala Leu Lys Asp Leu Lys Thr Ala Phe Ala Arg<br>              420                    425                    430 | 1296 |
| ttt att gat aac aag cag caa ttt ccc ctg gtg tac gac aat gta tgg<br>Phe Ile Asp Asn Lys Gln Gln Phe Pro Leu Val Tyr Asp Asn Val Trp<br>            435                    440                    445 | 1344 |
| aag gga gta gtg tct tcg gct agt tat gac ggt ggt gat tct ggg gct<br>Lys Gly Val Val Ser Ser Ala Ser Tyr Asp Gly Gly Asp Ser Gly Ala<br>            450                    455                    460 | 1392 |
| gat ttc gga aac aca tat tac aat gac cac cat ttt cac tac ggc tac<br>Asp Phe Gly Asn Thr Tyr Tyr Asn Asp His His Phe His Tyr Gly Tyr<br>465                    470                    475                    480 | 1440 |
| ttc atc cat gcc gct gca atc atc ggg tcc ctt gat cca tct tgg att<br>Phe Ile His Ala Ala Ala Ile Ile Gly Ser Leu Asp Pro Ser Trp Ile<br>                    485                    490                    495 | 1488 |
| caa ggc aac aaa gat tgg gtc aat atg ctt gtc cgt gat gca gga aat<br>Gln Gly Asn Lys Asp Trp Val Asn Met Leu Val Arg Asp Ala Gly Asn<br>              500                    505                    510 | 1536 |

```
gcc gct acc aat gat cca ctt ttc ccc ttt tct cgt ggg ttc gac tgg    1584
Ala Ala Thr Asn Asp Pro Leu Phe Pro Phe Ser Arg Gly Phe Asp Trp
        515                 520                 525 ttc cat ggt cat tca tgg gcg aaa ggg ctt ttt gaa tcc ttt gac ggg    1632
Phe His Gly His Ser Trp Ala Lys Gly Leu Phe Glu Ser Phe Asp Gly
        530                 535                 540 aaa gac gaa gag tcg aca tcg gaa gat gcg atg ttt gct tat gct cta    1680
Lys Asp Glu Glu Ser Thr Ser Glu Asp Ala Met Phe Ala Tyr Ala Leu
545                 550                 555                 560 aag atg tgg ggt aag acc att gga gat gcc agt atg gaa gca aga ggg    1728
Lys Met Trp Gly Lys Thr Ile Gly Asp Ala Ser Met Glu Ala Arg Gly
                565                 570                 575 aac ttg atg ctg ggc att ttg aga cgg agc ctc cat aat tat ttc ctc    1776
Asn Leu Met Leu Gly Ile Leu Arg Arg Ser Leu His Asn Tyr Phe Leu
            580                 585                 590 ttg gag gct gac aac aag aat cac ccc ccg gtc ttt gtt ccg aat aag    1824
Leu Glu Ala Asp Asn Lys Asn His Pro Pro Val Phe Val Pro Asn Lys
        595                 600                 605 gtg acg ggc ata tta ttc gaa aac aag gtg gac cac act acc tac ttt    1872
Val Thr Gly Ile Leu Phe Glu Asn Lys Val Asp His Thr Thr Tyr Phe
610                 615                 620 gga gcc aac cta gag tat att cac ggg att cac atg ctg ccg ctc tta    1920
Gly Ala Asn Leu Glu Tyr Ile His Gly Ile His Met Leu Pro Leu Leu
625                 630                 635                 640 ccg gtc tcg ccg tac aca cgc agc caa aag ttc gtc aag gaa gag tgg    1968
Pro Val Ser Pro Tyr Thr Arg Ser Gln Lys Phe Val Lys Glu Glu Trp
                645                 650                 655 gat gcc ctt ttt gca act aat gct gca gca ccg gcc gag cag gtg caa    2016
Asp Ala Leu Phe Ala Thr Asn Ala Ala Ala Pro Ala Glu Gln Val Gln
            660                 665                 670 gct gga tgg aaa ggt gtc tta tat gca aat ctt gcc ctt atc gat cca    2064
Ala Gly Trp Lys Gly Val Leu Tyr Ala Asn Leu Ala Leu Ile Asp Pro
        675                 680                 685 gtg tca gcc tgg aat ttc ttc gcg caa ccg aac ttc gac tat agc gtg    2112
Val Ser Ala Trp Asn Phe Phe Ala Gln Pro Asn Phe Asp Tyr Ser Val
690                 695                 700 atc gat ggg gga gcg aca cgg att tgg tac ctc gcg ctt gct gca ggt    2160
Ile Asp Gly Gly Ala Thr Arg Ile Trp Tyr Leu Ala Leu Ala Ala Gly
705                 710                 715                 720 gag tta acc acc cat tct tca ggg ttc att agc acc act aac aat ata    2208
Glu Leu Thr Thr His Ser Ser Gly Phe Ile Ser Thr Thr Asn Asn Ile
                725                 730                 735 tag                                                                2211
```

```
<210> SEQ ID NO 4
<211> LENGTH: 736
<212> TYPE: PRT
<213> ORGANISM: Aspergillus oryzae

<400> SEQUENCE: 4
```

```
Met Ala Thr Met Ala Asn Gly Gln Asp Val Phe Leu Pro Val Ser Thr
1               5                   10                  15

Gly Pro Ile Pro Gly Thr Val Lys Ser Arg Asn Asp His Pro Val Pro
                20                  25                  30

Arg Ala Ser Ile Met Asn Asn Thr Asp Pro Ile Glu Thr Asn Lys Phe
            35                  40                  45

Tyr Ala Gly Leu Phe Leu Gly Thr Gln Thr Asn Thr Thr Phe Thr His
        50                  55                  60
```

-continued

```
Pro Tyr Gly Ile Ala Trp Ala Lys Gly Asn Gly Asn Ala Lys Ser Tyr
 65                  70                  75                  80

Gly Met Ala Ile Ser His Ile Glu Ala Asp Lys Leu Ala Leu Gly Pro
                 85                  90                  95

Lys Asn Asp Lys Ile Pro Gly Ser Pro Val Gln Tyr Val Asn Pro
            100                 105                 110

Ile Gly Ile Gln Ser Ile Ile Leu Ser Ala Thr Glu Leu Gly Gly Ser
                115                 120                 125

Thr Val Leu Met Thr Glu Asn Pro Leu Pro Phe Ser Ala Asn Ala Val
        130                 135                 140

Leu Gln Pro Gln Ser Gly Ser Ser Glu Arg Ile Thr Phe Pro Val Val
145                 150                 155                 160

Gln Gly Met Gly Phe Val Thr Gly Ile Tyr Ser Asn Leu Gln Pro Val
                165                 170                 175

Ile Gln Ser Ser Val Phe Phe Ser Lys Val Ser Ala Gly Ser Pro
            180                 185                 190

Arg Pro Gly Ile Phe Lys Tyr Thr Val Asp Leu Ala Asp Gly Thr Asn
            195                 200                 205

Trp Leu Leu Tyr Leu Thr Ser Asn Asp Gly Lys Asp Pro Asn Leu His
    210                 215                 220

Leu Glu Ser Thr Thr Asn Leu Arg Gly Pro Pro Gly Trp Ser Gly Thr
225                 230                 235                 240

Val Gln Val Ala Lys Asn Pro Ala Gly Thr Leu Gly Glu Lys Leu Phe
                245                 250                 255

Asp Asn Ser Ser Gly Val Tyr Ala Thr Gln Gly Trp Val Lys Gly Ala
            260                 265                 270

Val Ser Gly Gln Thr Gly Thr Tyr Ser Leu Thr Trp Gly Lys Glu Gly
            275                 280                 285

Lys Asp Lys Asp Gly Thr Pro Leu Met Met Tyr Ala Leu Pro His His
290                 295                 300

Val Glu Ser Phe Asp Lys Thr Thr His Asp Arg Leu Thr Asn Ile Thr
305                 310                 315                 320

Met Arg Thr Thr Thr Lys Gly Asn Ala Thr Ala Val Ile Gly Glu Thr
                325                 330                 335

Trp Ser Met Val Glu Gln Asp Leu Pro Val Gly Met Gly Phe Ala Pro
            340                 345                 350

Trp Ser Val Ser Ala Gly Ser Val Asp Thr Ile Ser Pro Ala Ala Gln
            355                 360                 365

Lys Val Ile Ile Asp Val Ala Pro Thr Glu Leu Gln Gln Asp Val Gly
            370                 375                 380

Asn Gln Ser Asn Leu Asn Ser Met Tyr Tyr Ser Gly Lys Ala Leu Ser
385                 390                 395                 400

Lys Phe Ala Thr Leu Val Tyr Ala Val Asp Lys Leu Gly Gly Lys Pro
                405                 410                 415

Asp Leu Ala Ala Pro Ala Leu Lys Asp Leu Lys Thr Ala Phe Ala Arg
            420                 425                 430

Phe Ile Asp Asn Lys Gln Gln Phe Pro Leu Val Tyr Asp Asn Val Trp
        435                 440                 445

Lys Gly Val Val Ser Ser Ala Ser Tyr Asp Gly Gly Asp Ser Gly Ala
    450                 455                 460

Asp Phe Gly Asn Thr Tyr Tyr Asn Asp His His Phe His Tyr Gly Tyr
465                 470                 475                 480

Phe Ile His Ala Ala Ala Ile Ile Gly Ser Leu Asp Pro Ser Trp Ile
```

```
                        485                 490                 495
Gln Gly Asn Lys Asp Trp Val Asn Met Leu Val Arg Asp Ala Gly Asn
            500                 505                 510
Ala Ala Thr Asn Asp Pro Leu Phe Pro Phe Ser Arg Gly Phe Asp Trp
        515                 520                 525
Phe His Gly His Ser Trp Ala Lys Gly Leu Phe Glu Ser Phe Asp Gly
    530                 535                 540
Lys Asp Glu Glu Ser Thr Ser Glu Asp Ala Met Phe Ala Tyr Ala Leu
545                 550                 555                 560
Lys Met Trp Gly Lys Thr Ile Gly Asp Ala Ser Met Glu Ala Arg Gly
                565                 570                 575
Asn Leu Met Leu Gly Ile Leu Arg Arg Ser Leu His Asn Tyr Phe Leu
            580                 585                 590
Leu Glu Ala Asp Asn Lys Asn His Pro Pro Val Phe Val Pro Asn Lys
        595                 600                 605
Val Thr Gly Ile Leu Phe Glu Asn Lys Val Asp His Thr Thr Tyr Phe
    610                 615                 620
Gly Ala Asn Leu Glu Tyr Ile His Gly Ile His Met Leu Pro Leu Leu
625                 630                 635                 640
Pro Val Ser Pro Tyr Thr Arg Ser Gln Lys Phe Val Lys Glu Glu Trp
                645                 650                 655
Asp Ala Leu Phe Ala Thr Asn Ala Ala Ala Pro Ala Glu Gln Val Gln
            660                 665                 670
Ala Gly Trp Lys Gly Val Leu Tyr Ala Asn Leu Ala Leu Ile Asp Pro
        675                 680                 685
Val Ser Ala Trp Asn Phe Phe Ala Gln Pro Asn Phe Asp Tyr Ser Val
    690                 695                 700
Ile Asp Gly Gly Ala Thr Arg Ile Trp Tyr Leu Ala Leu Ala Ala Gly
705                 710                 715                 720
Glu Leu Thr Thr His Ser Ser Gly Phe Ile Ser Thr Thr Asn Asn Ile
                725                 730                 735
```

<210> SEQ ID NO 5
<211> LENGTH: 30
<212> TYPE: DNA
<213> ORGANISM: Artificial Sequence
<220> FEATURE:
<223> OTHER INFORMATION: Synthetic primer sequence derived from the base
      sequence of a putative exo-b-1,3-glucanase gene of Aspergillus
      oryzae

<400> SEQUENCE: 5
atggagggct ccgatgcaca accgccgttc                                    30

<210> SEQ ID NO 6
<211> LENGTH: 30
<212> TYPE: DNA
<213> ORGANISM: Artificial Sequence
<220> FEATURE:
<223> OTHER INFORMATION: Synthetic primer sequence derived from the base
      sequence of a putative exo-b-1,3-glucanase gene of Aspergillus
      oryzae

<400> SEQUENCE: 6
ttaataatat tccggtaaat ccccgaaact                                    30

<210> SEQ ID NO 7
<211> LENGTH: 30
<212> TYPE: DNA

```
<213> ORGANISM: Artificial Sequence
<220> FEATURE:
<223> OTHER INFORMATION: Synthetic primer sequence derived from the base
      sequence of a putative endo-b-1,3-glucanase gene of Aspergillus
      oryzae

<400> SEQUENCE: 7
atggcgacaa tggcaaacgg tcaagatgtg                                    30

<210> SEQ ID NO 8
<211> LENGTH: 30
<212> TYPE: DNA
<213> ORGANISM: Artificial Sequence
<220> FEATURE:
<223> OTHER INFORMATION: Synthetic primer sequence derived from the base
      sequence of a putative endo-b-1,3-glucanase gene of Aspergillus
      oryzae

<400> SEQUENCE: 8
ctatatattg ttagtggtgc taatgaaccc                                    30

<210> SEQ ID NO 9
<211> LENGTH: 29
<212> TYPE: DNA
<213> ORGANISM: Artificial Sequence
<220> FEATURE:
<223> OTHER INFORMATION: Synthetic primer based on the exo-b-1,
      3-glucanase gene

<400> SEQUENCE: 9
ctagctagca tggagggctc cgatgcaca                                     29

<210> SEQ ID NO 10
<211> LENGTH: 29
<212> TYPE: DNA
<213> ORGANISM: Artificial Sequence
<220> FEATURE:
<223> OTHER INFORMATION: Synthetic primer based on the exo-b-1,
      3-glucanase gene

<400> SEQUENCE: 10
ccgctcgaga taatattccg gtaaatccc                                     29

<210> SEQ ID NO 11
<211> LENGTH: 29
<212> TYPE: DNA
<213> ORGANISM: Artificial Sequence
<220> FEATURE:
<223> OTHER INFORMATION: Synthetic primer based on the endo-b-1,
      3-glucanase gene

<400> SEQUENCE: 11
ctagctagca tggcgacaat ggcaaacgg                                     29

<210> SEQ ID NO 12
<211> LENGTH: 30
<212> TYPE: DNA
<213> ORGANISM: Artificial Sequence
<220> FEATURE:
<223> OTHER INFORMATION: Synthetic primer based on the endo-b-1,
      3-glucanase gene

<400> SEQUENCE: 12
ccgctcgagg ttagtggtgc taatgaaccc                                    30

<210> SEQ ID NO 13
<211> LENGTH: 29
```

```
<212> TYPE: DNA
<213> ORGANISM: Artificial Sequence
<220> FEATURE:
<223> OTHER INFORMATION: Synthetic primer based on the endo-b-1,
      3-glucanase gene

<400> SEQUENCE: 13
ctagctagca tggcgacaat ggcaaacgg                                        29

<210> SEQ ID NO 14
<211> LENGTH: 30
<212> TYPE: DNA
<213> ORGANISM: Artificial Sequence
<220> FEATURE:
<223> OTHER INFORMATION: Synthetic primer based on the endo-b-1,
      3-glucanase gene

<400> SEQUENCE: 14
ggactagtct atatattgtt agtggtgcta                                       30
```

GENES OF CELL WALL-DEGRADING ENZYMES DERIVED FROM ASPERGILLUS, AND METHOD FOR THE PRODUCTION THE ENZYMES

TECHNICAL FIELD

The present invention relates to a gene or DNA encoding novel enzymes having β-1,3-glucanase activity (exo-, or endo-β-1,3-glucanase), a recombinant expression vector comprising them, a microorganism having the recombinant expression vector, the novel enzymes having β-1,3-glucanase activity, and a method for the production of said enzymes.

BACKGROUND OF THE INVENTION

β-1,3-glucan is considered to activate a cell involved in an immune system in a body. It is therefore used as an anticancer agent in an injection form. It has been confirmed that β-1,3-glucan circulates through blood vessels and stimulates immune competent cells in organs such as liver so that it will enhance the immune system in the body (Sugawara et al., Cancer. Immunol. Immunother. 16:137, 1984). However, an intact 13-1,3-glucan having a high molecular weight shows little effect, and only after being reduced in molecular weight, it will able to show an anti-cancer activity (Kojima et al., Agric. Biol. Chem. 50:231-232,1986).

β-1,3-glucan is conventionally reduced in molecular weight by means of acid, heat, or sonication. However, the safety of the reduction in molecular weight by partial hydrolysis with acid can not be guaranteed because it uses a substance that is unfavorable to a human body such as formic acid. Furthermore, such degradation has disadvantages such as that it will require a stringent treatment in order to equalize the molecular weight. On the other hand, the sonication used in the production of "Sonifiran", which is commercially available as a medical product, has a cost problem.

As *Aspergillus* is listed as Generally Recognized as Safe (GRAS) in Department of Agriculture in USA (USDA), enzymes produced by *Aspergillus* have a high safety when they are added in foods. *Aspergillus oryzae* is also a very safe microorganism to the human body, as it has been also used for a long time in fermentation, brewing, the production of enzymes, etc.

SUMMARY OF THE INVENTION

The present inventors have studied in order to find novel enzymes having β-1,3-glucan-degrading activity (exo-, and endo-β-1,3-glucanase) from such safe *Aspergillus oryzae* species.

Thus, the purpose of the present invention is to isolate a gene encoding novel exo-, or endo-1-1,3-glucanase. Further, the purpose of the present invention is to obtain a recombinant expression vector comprising said gene, a microorganism transformed with said vector (transformant), and a microorganism having an enhanced expression of said gene. Still further, the purpose of the present invention is to degrade β-1,3-glucan to its low molecular weight form by means of said enzymes.

Focusing attention on the advantages of *Aspergillus oryzae*, the present inventors have tried to isolate the gene encoding β-1,3-glucanase from *Aspergillus oryzae* and to construct a safe and simple system for the molecular weight reduction of β-1,3-glucan, and finally completed the present invention.

Thus, the present inventors have succeeded in searching the genes of exo-, and endo-β-1,3-glucanase from *Aspergillus oryzae*, determining the base sequences of said genes and further producing the tranformant comprising said gene introduced therein, and expressing of exo-, and endo-β-1,3-glucanase.

The first aspect of the present invention relates to the following genes (1) and (2):
(1) a gene encoding one of the following proteins:
   (a) β-1,3-glucanase derived from *Aspergillus oryzae* and having a molecular weight of 62 kD,
   (b) a protein consisting of an amino acid sequence represented by SEQ ID No.2,
   (c) a protein consisting of the amino acid sequence represented by SEQ ID No.2 wherein one or several amino acid residues are replaced, deleted, inserted or transferred, and having exo-β-1,3-glucanase activity, and
   (d) a protein comprising an amino acid sequence having identity of 80% or more to the amino acid sequence represented by SEQ ID No.2 or a partial fragment thereof, and having exo-β-1,3-glucanase activity.
(2) A gene comprising one of the following DNAs:
   (a) DNA consisting of a base sequence represented by SEQ ID No.1,
   (b) DNA being hybridized with a nucleic acid comprising the base sequence represented by SEQ ID No.1 or its complementary chain under stringent conditions, and encoding a protein having exo-β-1,3-glucanase activity, and
   (c) DNA having identity of 80% or more to DNA of the base sequence represented by SEQ ID No.1 or a partial fragment thereof, and encoding the protein having exo-β-1,3-glucanase activity.

The above genes encode a protein having exo-β-1,3-glucanase activity.

The second aspect of the present invention relates to the following genes (3) and (4):
(3) A gene encoding one of the following proteins:
   (a) β-1,3-glucanase derived from *Aspergillus oryzae* and having a molecular weight of 80 kD,
   (b) a protein consisting of an amino acid sequence represented by SEQ ID No.4,
   (c) a protein consisting of the amino acid sequence represented by SEQ ID No.4 wherein one or several amino acid residues are replaced, deleted, inserted or transferred, and having endo-β-1,3-glucanase activity, and
   (d) a protein comprising an amino acid sequence having identity of 80% or more to the amino acid sequence represented by SEQ ID No.4 or a partial fragment thereof, and having endo-β-1,3-glucanase activity.
(4) A gene comprising one of the following DNAs:
   (a) DNA consisting of a base sequence represented by SEQ ID No.3,
   (b) DNA being hybridized with a nucleic acid comprising the base sequence represented by SEQ ID No.3 or its complementary chain under stringent conditions, and encoding a protein having endo-β-1,3-glucanase activity, and
   (c) DNA having identity of 80% or more to DNA of the base sequence represented by SEQ ID No.3 or a partial fragment thereof, and encoding the protein having endo-β-1,3-glucanase activity.

The above genes encode a protein having endo-β-1,3-glucanase activity.

The third aspect of the present invention relates to a recombinant expression vector comprising any one of the above genes, to a microorganism having said recombinant expression vector, and to a method for the production of exo-, or endo-β-1,3-glucanase, comprising culturing said microorganism in a culture medium, collecting the exo-, or endo-β-1,3-glucanase from culture material.

Further, the present invention relates to one of the following proteins:
(a) β-1,3-glucanase derived from *Aspergillus oryzae* and having a molecular weight of 62 kD,
(b) a protein consisting of an amino acid sequence represented by SEQ ID No.2,
(c) a protein consisting of the amino acid sequence represented by SEQ ID No.2 wherein one or several amino acid residues are replaced, deleted, inserted or transferred, and having exo-β-1,3-glucanase activity, and
(d) a protein comprising an amino acid sequence having identity of 80% or more to the amino acid sequence represented by SEQ ID No.2 or a partial fragment thereof, and having exo-β-1,3-glucanase activity.

The above proteins have exo-β-1,3-glucanase activity.

Further, the present invention relates to one of the following proteins:
(a) β-1,3-glucanase derived from *Aspergillus oryzae* and having a molecular weight of 80 kD,
(b) a protein consisting of an amino acid sequence represented by SEQ ID No.4,
(c) a protein consisting of the amino acid sequence represented by SEQ ID No.4 wherein one or several amino acid residues are replaced, deleted, inserted or transferred, and having endo-β-1,3-glucanase activity, and
(d) a protein comprising an amino acid sequence having identity of 80% or more to the amino acid sequence represented by SEQ ID No.4 or a partial fragment thereof, and having endo-β-1,3-glucanase activity.

The above proteins have endo-β-1,3-glucanase activity.

Those proteins may be purified from *Aspergillus oryzae* by any method known to those skilled in the art, or may be obtained as a recombinant protein by the above method.

The present invention still further relates to a food comprising the microorganism having the recombinant expression vector or its culture material and/or the protein according to the present invention. In the food according to the present invention, the β-1,3-glucanase activity of the protein of the present invention will promote the reduction of the molecular weight of β-1,3-glucan contained in the food.

Thus, the present invention relates also to a method for the production of low molecular weight β-1,3-glucan, comprising reacting the above microorganism or its culture material and/or the protein of the present invention with β-1,3-glucan. Such reaction may be easily accomplished by making each of the above substances exist in the food containing β-1,3-glucan or in a suitable system comprising β-1,3-glucan so as to cause an enzyme reaction.

The present invention has revealed the genes and amino acid sequences of the novel endo-, or exo-β-1,3-glucanase derived from *Aspergillus oryzae*. It has been also confirmed that the microorganism transformed with the recombinant expression vector comprising those genes has P-1,3-glucanase activity.

Further, the endo-β-1,3-glucanase was purified from transformed *E. coli* and identified with respect to characteristics such as substrate-specificity, optimum pH value, pH stability, optimum temperature, thermal stability (heat-stability), and specific activity, and confirmed to be an endo-type enzyme by HPLC.

BRIEF DESCRIPTION OF THE INVENTION

Figure 3:
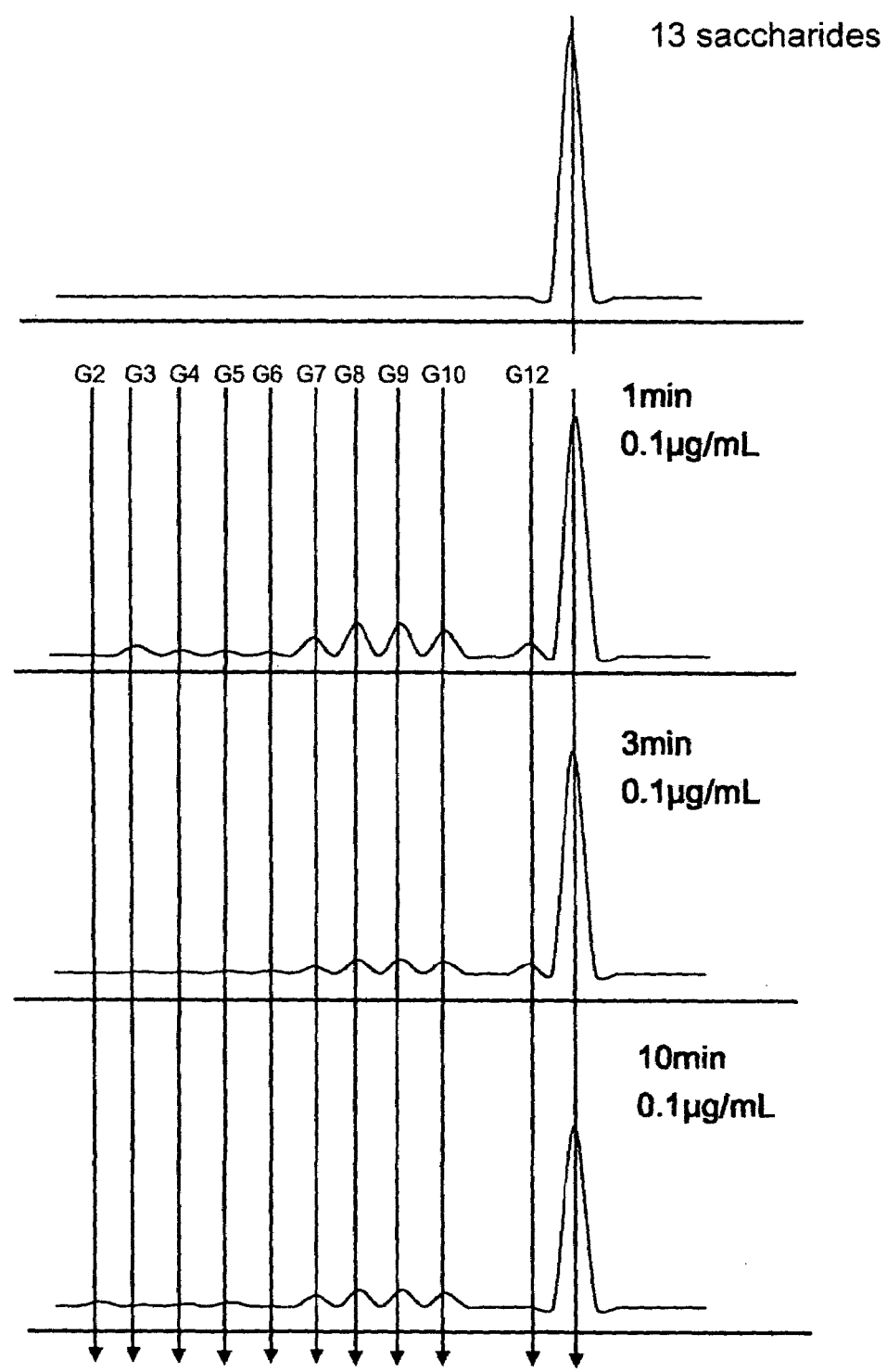
Figure 4:
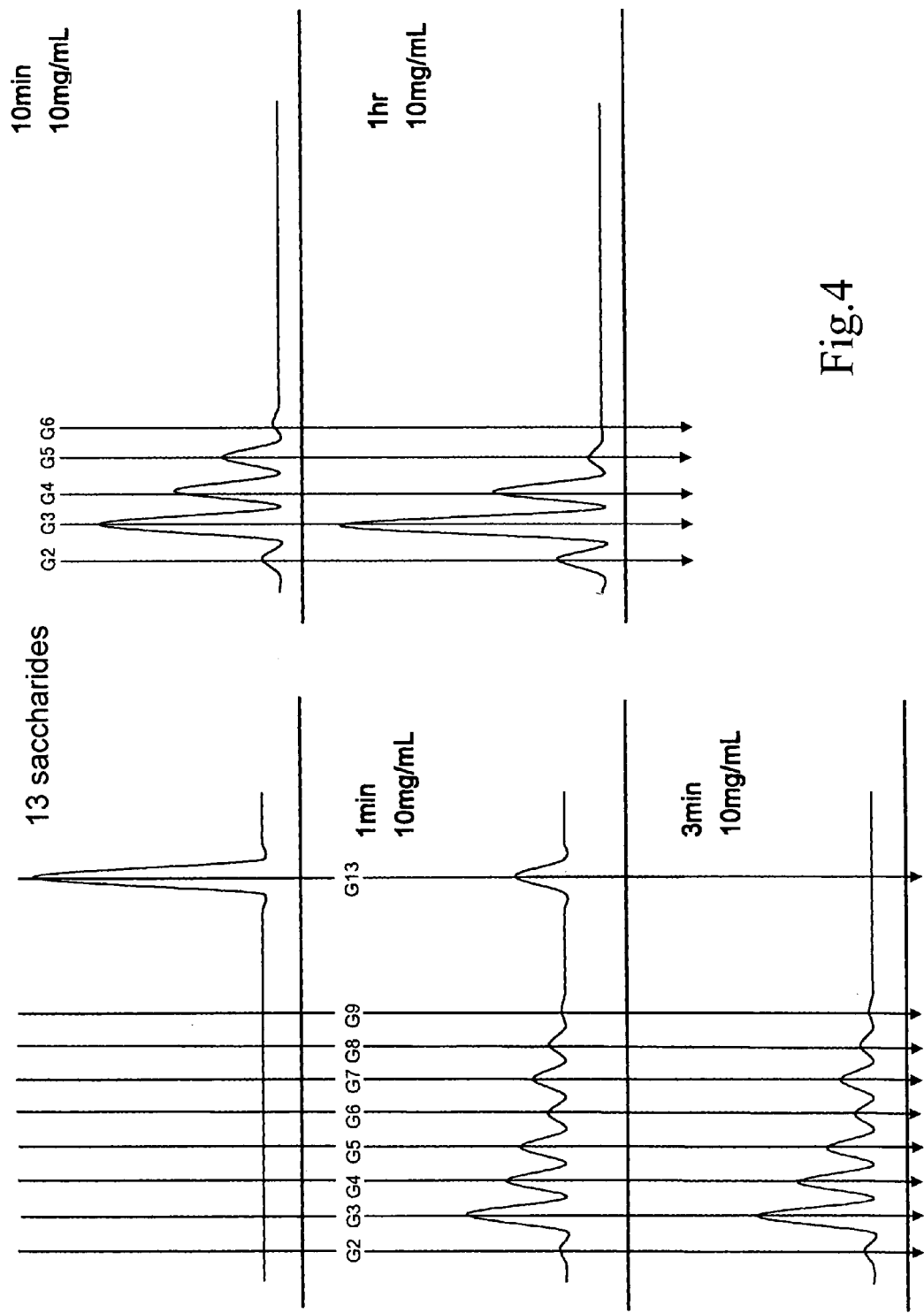

FIG. 1 shows briefly the construction method of a plasmid.
FIG. 2 shows the results of SDS-PAGE (10%) of the expressed proteins of the present invention, by using a sample prepared by collecting cells that were induced with IPTG or not, and disrupted by sonication.
FIG. 3 is a chart showing the results obtained from. HPLC analysis of laminarioligosaccharide having 13 saccharides treated with endo-β-1,3-glucanase (0.1 µg/ml).
FIG. 4 is a chart showing the results obtained from HPLC analysis of laminarioligosaccharide having 13 saccharides treated with endo-β-1,3-glucanase (10 µg/ml).

THE BEST MODE OF THE PRESENT INVENTION

The Genes According to the Present Invention:
Sequence information obtained from the genome analysis of *Aspergillus oryzae* is applied to BLAST search to obtain the information about the novel exo-, and endo-β-1,3-glucanase genes. A total RNA is extracted from *Aspergillus oryzae* RIB40 strain (ATCC 42149) based on the above information, and mRNA is then purified and subjected to RT-PCR to amplify cDNA. The resulting cDNA fragments are cloned into a vector and sequenced to determine its translated region.

The genes according to the present invention may be prepared by any method known to those skilled in the art. For example, suitable primers are synthesized on the basis of the information about the base or amino acid sequences of the present genes described in the present specification. The genes may be amplified by PCR by using the above primers and a suitable cDNA library prepared from the total RNA of *Aspergillus oryzae* by any method known to those skilled in the art.

PCR may be carried out in accordance with conditions and means known to those skilled in the art by using a primer set for amplification according to the present invention. For example, the PCR is done by heating for 2 min at 94° C., followed by repeating 30 times a cycle of heating for 10 seconds at 94° C., for 20 seconds at 55° C., and for 2 min. at 72° C., and finally by for 5 min at 72° C. A usual thermal cycler such as a "9600" model manufactured by Perkin Elmer Co. may be used. A commercially available thermal resistance DNA polymerase such as ExTaq DNA polymerase (TAKARA SHUZO CO., LTD.) may be used, and the composition of a reaction mixture may be adjusted in accordance with manufacturer's instructions attached to the above polymerase product.

Alternatively, the genes according to the present invention may be obtained by screening the cDNA library by means of hybridization with a suitable probe prepared on the above base sequence. Furthermore, the genes according to the present invention may be prepared by a chemical synthesis method well known to those skilled in the art.

The term "stringent conditions" means in this specification, for example, those of sodium concentration of 150~900 mM, preferably 600~900 mM, pH of 6~8 at 60° C.~68° C.

A representative example of DNA that is hybridized under stringent conditions according to the present invention includes, for example, DNA or its fragments having a high identity between each base sequence, such as those having a sequence identity of about 80% or more, preferably about 90% or more, more preferably about 95% or more on a total average, and encoding a protein having a particular β-1,3-glucanase activity. The identity between the base sequences may be determined by means of algorithm known to those skilled in the art, such as BLAST that is used in an example of the present specification.

The hybridization may be performed in accordance with a method known in the art, for example, that described in Current protocols in molecular biology (edited by Frederick M. Ausubel et al., 1987). When a commercially available library is used, the hybridization may be done according to instructions attached to it.

The Proteins According to the Present Invention:

The protein consisting of an amino acid sequence wherein one or several amino acid residues are replaced, deleted, inserted or transferred, and having a particular β-1,3-glucanase activity may be easily prepared by any combination of methods known to those skilled in the art, such as site-specific mutagenesis, homologous recombination, primer extension method, and PCR.

Replacement between amino acids belonging to the same group (polar or non-polar amino acids, hydrophobic or hydrophilic amino acids, positively- or negatively charged amino acids, aromatic amino acids, etc.) may be selected in order to maintain substantially the same function as that of the original protein. On the other hand, amino acids within a functional domain of the protein should preferably be kept for the above purpose.

The protein according to the present invention further includes a protein or its fragment having a high identity such as about 80% or more, preferably about 90% or more, more preferably about 95% or more on a total average to the amino acids sequences disclosed in the present specification and having a particular β-1,3-glucanase activity. The identity between the amino acid sequences may be also determined by means of algorithm known to those skilled in the art, such as BLAST that is used in the example of the present specification. The activity of β-1,3-glucanase may be measured by a method described in the example of the present specification.

The Expression of the Genes According to the Present Invention

The thus obtained genes according to the present invention may be integrated into a recombinant vector by any method known to those skilled in the art to give a recombinant expression vector according to the present invention. For example, the recombinant expression vector may be prepared by (1) excising a DNA fragment containing the gene according to the present invention, (2) inserting the DNA fragment into a restriction site or multi-cloning site in an appropriate recombinant vector to ligate it to the vector. There is no limitation on the recombinant vector, which includes plasmids derived from *Aspergillus* such as pSa123, pTAex3, pNGU113, pRBG1, pGM32, pSE52, and pNAGL142; plasmids derived from *E. coli* such as pT7Blue T-Vector, pRSET, pBR322, pBR325, pUC18 and pUC118; plasmids derived from *Bacillus* such as pUB110, pTP5, and pU194; and plasmids derived from yeast such as pSH19 and pSH15.

The above recombinant expression vector may optionally contain various known transcription regulating elements such as promoter, Shine-Dalgarno sequence, a selective marker, and a transcription termination signal, as long as they do not interfere with the activity of a transcription regulating sequence. If desired, the protein encoded by the gene according to the present invention may be expressed as a fusion protein with other protein or peptide, for example, glutathione S-transferase, histidine tag, calmodulin-binding protein, and protein A. Such fusion protein may be cleaved by an appropriate protease into each protein.

There is no limitation on the kind and source of a host cell to be used in the production of the microorganism having the recombinant expression vector according to the present invention (transformant), as long as the gene of the present invention may be effectively expressed. When the microorganism having the recombinant expression vector or its culture material and/or the protein according to the present invention is added to a food, it is preferable to use as the host cell a microorganism that is known to be highly safe to the human body, such as *Aspergillus*, *Saccharomyces cerevisiae* (bread yeast), and *Bacillus subtilis*. Further, the following microorganisms, which are listed as GRAS, may be used in the present invention: *Pseudomonas fluorescens*, *Laminaria japonica*, *Fusarium oxysporum*, *Streptoverticillium mobaraense*, *Kluyveromyces marxianus*, *Candida rugosa*, *Streptoverticillium mobaraense*, *Thermomyces lanuginosus*, *Aspergillus sojae*, and, *Aspergillus aculeatus*.

The transformation of the above host cells may be carried out in accordance with a method known in the art such as calcium chloride method, particle gun, and electroporation. Reference may be made to, for example, Proc. Natl. Acad. Sci. USA, 69, 2110, (1972); Gene, Vol. 17, 107(1982); Molecular & General Genetics, Vol. 168, 111 (1979); Methods in Enzymology, Vol. 194 182-187 (1991); Proc. Natl. Acad. Sci. USA, Vol. 75, 1929 (1978); Cell Technology, Additional volume No.8, New Protocol of Cell Technology Experiment, 263-267 (1995), published by Shujunsya Co., Ltd.; and Virology, Vol. 52, 456 (1973).

The thus obtained transformant of the present invention may be cultured in accordance with a method known in the art.

Any method known in the art may be optionally used in the production of the protein of the present invention. For example, it may be separated and purified as a substantially pure and homogenous protein from the culture medium containing the protein by an optional combination of methods known to those skilled in the art such as various kinds of chromatography, filtration, ultrafiltration, salting out, precipitation with solvent, extraction with solvent, evaporation, immuno-precipitation, SDS-polyacrylamide electrophoresis, isoelectric focusing electrophoresis, dialysis, and re-crystalization.

When the protein is expressed as the fusion protein with glutathione S-transferase or several histidine tags, it may be purified by means of a glutathione column or a nickel column. After the purification of the fusion protein, regions other than the desired protein may be cleaved and removed, if desired, by thrombin, Factor Xa, etc. Alternatively, the protein may be treated with an appropriate protein-modifying enzyme such as trypsin, chymotrpsin, lysylendopeptidase, proteinkinase and glucosidase before or after the purification so as to optionally modify the protein, or to partially remove a peptide from the protein.

The present invention will be specifically explained below with reference to the examples, which should not be construed to limit the scope of the present invention.

EXAMPLE 1

Amplification of cDNA of exo-β-1,3-glucanase from *Aspergillus oryzae* and Determination of its Base Sequence The cDNA of the gene of the present invention was amplified by using RT-PCR and its base sequence was determined. Spore of an *Aspergillus oryzae* RIB40 strain (ATCC 42149) was cultured with shaking in 100 ml of YPD medium (1% yeast extract, 2% bactopeptone, 2% glucose, 0.5% mono-potassium phosphate, 0.05% magnesium sulfate) for 20 hours at 30° C. Fungi (mycelium) were then transferred to an oligotrophic medium (0.3% sodium nitrate, 0.1% mono-potassium phosphate, 0.2% potassium chloride, 0.05% magnesium sulfate, 4% sodium chloride) and cultured therein further for 6 hours at 30° C. After collecting the fungi the total RNA was obtained in accordance with a method of Chigwin et al., Biochemistry 18, 5294-5299, 1979, followed by purification of mRNA with oligo (dT) cellulose column (Amersham Co.). The first strand cDNA was synthesized by a reverse transcription by using oligo (dT)$_{12-18}$ primers (Invitrogen Co.) as a primer and SuperScript II RNaseH-Reverse Trascriptase as a reverse transcription enzyme. A full-length cDNA was then obtained by PCR by using the resulting first strand cDNA as a template.

Next, the following two primers were prepared based on the information about a base sequence of a putative exo-β-1,3-glucanase gene of *Aspergillus oryzae*, which had been deduced by applying the information about the DNA sequence obtained from genome analysis of the *Aspergillus oryzae* RIB40 strain to NCBI blastx (NCBI blastx (http://www.ncbi.nlm.nih.gov/BLASX/):

5'-ATGGAGGGCTCCGATGCACAACCGCCGTTC-3' (SEQ ID No.5)

5'-TTAATAATATTCCGGTAAATCCCCGAAACT-3' (SEQ ID No.6)

PCR was done with Expand HF (Roche Diagnostics K.K.) and by means of DNA Thermal Cycler (TAKARA SHUZO CO., LTD.). The composition of a reaction solution used in this example was as follows:

TABLE 1

| | |
|---|---|
| H$_2$O | 34 μl |
| 10 × Reaction Buffer: | 5 μl 1x |
| 2.5 mM dNTP, Mix: | 5 μl (250 μM) |
| Primer: | 1 μl 2x (20 μM) |
| Template: | 3 μl |
| Expand HF DNA polymerase mix: | 1 μl (3.5 U/TEST) |
| A total liquid volume: | 50 μl |

The above reaction solution (50 μl) was mixed in a reaction tube (0.2 ml) and set in the DNA Thermal Cycler to be subjected to PCR with the following temperature conditions:
94° C. for 3 minutes, 1 cycle;
94° C. for 1 minute, 55° C. for 2 minutes, 72° C. for 2 minutes, 30 cycles; and
72° C. for 7 minutes, 1 cycle.

An amplified product was identified with 1.0% agarose gel electrophoresis. A DNA fragment was isolated and purified in the gel electrophoresis, ligated with TA cloning vector pT7Blue T-Vector (Novagen Co.) and cloned into *E. coli* JM109 strain (Nippon Gene Co. Ltd.). A plasmid was prepared from the resulting clone, and a base sequence of the cloned DNA fragment was analyzed. A missing part, when compared with a base sequence of the genomic DNA determined by the *Aspergillus* genome analysis, was identified as an intron.

The determination of the base sequence of the above cDNA revealed an open reading frame (ORF) consisting of 1650 bp, which is shown as SEQ ID No.1. Comparison between the genomic DNA sequence obtained from the *Aspergillus* genome analysis and the cDNA sequence of the present DNA confirmed that the genomic DNA had two introns consisting of 52 bp and 74 bp, respectively. An amino acid sequence deduced from the above base sequence is shown as SEQ ID No.2. A sequence having a high identity to said amino acid sequence was searched on known amino acid sequence data base. As a result, there was no identical amino acid sequence found, but it was confirmed that ExgH protein of *Shizosaccharomyces pommbe* (Accession Q10444) had the highest identity (about 42.4%) to said amino acid sequence, leading to the conclusion that the above gene was AoexgH gene.

EXAMPLE 2

Amplification of cDNA of endo-β-1,3-glucanase from *Aspergillus oryzae* and Determination of its Base Sequence The cDNA of the gene of the present invention was amplified by using RT-PCR and its base sequence was determined. Spore of the *Aspergillus oryzae* RIB40 strain was cultured with shaking in 100 ml of the above YPD medium for 20 hours at 30° C. Fungi (mycelium) were then transferred to the oligotrophic medium and cultured therein further for 6 hours at 30° C. After collecting the fungi, total RNA was obtained in accordance with a method of Chigwin et al., Biochemistry 18, 5294-5299, 1979, followed by purification of mRNA with oligo (dT) cellulose column (Amersham Co.). The first strand cDNA was synthesized by a reverse transcription by using oligo (dT)$_{12-18}$ primer (Invitrogen Co.) as a primer and SuperScript II RNaseH-Reverse Trascriptase as a reverse transcription enzyme. A full-length cDNA was then obtained by PCR by using the resulting first strand cDNA as a template.

Next, in a similar way to Example 1, the following two primers were prepared based on the information about the base sequence of a putative endo-β-1,3-glucanase gene of *Aspergillus oryzae*:

5'-ATGGCGACAATGGCAAACGGTCAAGATGTG-3' (SEQ ID No.7)

5'-CTATATATTGTTAGTGGTGCTAATGAACCC-3' (SEQ ID No.8)

PCR was done with the Expand HF and by means of the DNA Thermal Cycler. The composition of a reaction solution used in this example was as follows:

TABLE 2

| | |
|---|---|
| H$_2$O | 34 μl |
| 10 × Reaction Buffer: | 5 μl 1x |
| 2.5 mM dNTP, Mix: | 5 μl (250 μM) |
| Primer: | 1 μl 2x (20 μM) |
| Template: | 3 μl |
| Expand HF DNA polymerase mix: | 1 μl (3.5 U/TEST) |
| A total liquid volume: | 50 μl |

The above reaction (50 µl) was mixed in a reaction tube (0.2 ml) and set in the DNA Thermal Cycler to be subjected to PCR with the following temperature conditions:
94° C. for 3 minutes, 1 cycle;
94° C. for 1 minute, 50° C. for 2 minutes, 72° C. for 2 minutes, 35 cycles; and
72° C. for 7 minutes, 1 cycle.

An amplified product was identified with 1.0% agarose gel electrophoresis. A DNA fragment was isolated and purified in the gel electrophoresis, ligated with the TA cloning vector pT7Blue T-Vector and cloned into the E. coli JM109 strain. A plasmid was prepared from the resulting clone, and a base sequence of the cloned DNA fragment was analyzed. A missing part, when compared with the base sequence of the genomic DNA determined by the Aspergillus genome analysis, was identified as an intron.

The determination of the base sequence of the above cDNA revealed an open reading frame consisting of 2211 bp, which is shown as SEQ ID No.3. Comparison between the genomic DNA sequence obtained from the Aspergillus genome analysis and the cDNA sequence of the present DNA confirmed that the genomic DNA had three introns consisting of 55 bp, 50 bp and 79 bp, respectively. An amino acid sequence deduced from the above base sequence is shown as SEQ ID No.4. A sequence having a high identity to said amino acid sequence was searched on known amino acid sequence data base. As a result, there was no identical amino acid sequence found, but it was confirmed that EngL1 protein of Aspergillus fumigatus (Accession AF121133) had the highest identity (about 74%) to said amino acid sequence, leading to the conclusion that the above gene was AoengL gene.

EXAMPLE 3

Expression of the Novel exo-β-1,3-glucanase Gene in E. coli

PCR reaction was carried out by using the cDNA obtained above as a template to give a DNA fragment comprising an ORF of the novel exo-β-1,3-glucanase gene. The following two base sequences prepared based on the base sequence of said gene were used as primers:

5'-CTAGCTAGCATGGAGGGCTCCGATGCACA-3'  (SEQ ID No.9)

5'-CCGCTCGAGATAATATTCCGGTAAATCCC-3'  (SEQ ID No.10)

Each primer was modified to have NheI recognition site at its 5' end, and XhoI recognition site at its 3' end.

PCR was done with Expand HF and by means of the DNA Thermal Cycler. The composition of a reaction solution used in this example was as follows:

TABLE 3

| H$_2$O | 34 µl |
| 10 × Reaction Buffer: | 5 µl 1x |
| 2.5 mM dNTP, Mix: | 5 µl (250 µM) |
| Primer: | 1 µl 2x (20 µM) |
| Template: | 3 µl |
| Expand HF DNA polymerase mix: | 1 µl (3.5 U/TEST) |
| A total liquid volume: | 50 µl |

The above reaction solution (50 µl) was mixed in a reaction tube (0.2 ml) and set in the DNA Thermal Cycler to be subjected to PCR with the following temperature conditions:

94° C. for 3 minutes, 1 cycle;
94° C. for 1 minute, 50° C. for 2 minutes, 72° C. for 2 minutes, 25 cycles; and
72° C. for 7 minutes, 1 cycle.

An amplified product was identified with 1.0% agarose gel electrophoresis. A DNA fragment was isolated and purified in the gel electrophoresis, ligated with the TA cloning vector pT7Blue T-Vector and cloned into the E. coli JM109 strain. A plasmid was prepared from the resulting clone, and the base sequence of the cloned DNA fragment was confirmed. As a result, one cloning plasmid having no error was obtained, and it was digested with NheI and XhoI. A digested DNA fragment was identified with 1.0% agarose gel electrophoresis and collected. The collected DNA fragment was ligated with pET-21 b(+) (Novagen Co.) digested with NheI and XhoI (FIG. 1), and E. coli BL21-CodonPlus (DE3)-RIL strain (Stratagene Co.) was transformed with the resulting vector. The plasmid was obtained from 16 transformant clones and analyzed about the presence of the thus inserted DNA fragment to confirm that 4 clones out of them had it therein.

The above E. coli transformant was cultured with shaking for 20 hours at 20° C. in a culture medium (1% tryptone, 0.5% yeast extract, 1% sodium chloride, 50 µg/ml ampicillin, 0.1 mM IPTG) containing a 1/10 volume of the medium used for culture overnight. The tranformants were harvested, disrupted with an ultrasonic disintegrator (COSMO BIO CO., LTD) and subjected to SDS-polyacrylamide gel electrophoresis, which showed the existence of a protein with a molecular weight of 62 kDa (FIG. 2-A).

The above disrupted cells were centrifuged and the resulting supernatant was subjected to purification with His MicroSpin Purification Module (Amersham Pharmacia Co.), followed by measurement of the activity of β-1,3-glucanase.

The above measurement was carried out with a reaction time of one hour according to Rachel et al. (Gene 226, 147-154 (1999)) by using laminarin (Sigma Co.) as a substrate. The results are shown in Table 5. The activity of β-1,3-glucanase was found in the above E. coli transformant showing that β-1,3-glucanase had been produced by the same transformant, while no activity was detected in E. coli transformed by the vector pET-21 b(+) alone.

The plasmid pExgH prepared from the above transformant was deposited at the International Patent Organism Depository of National Institute of Advanced Industrial Science and Technology on Jun. 24, 2004 with an acceptance No. FERM AP-20100.

EXAMPLE 4

Expression of the Novel endo-β-1.3-glucanase Gene in E. coli

PCR reaction was carried out by using the cDNA obtained above as a template to give a DNA fragment comprising an ORF of the novel endo-β-1,3-glucanase gene. The following two base sequences prepared based on the base sequence of said gene were used as primers:

5'-CTAGCTAGCATGGCGACAATGGCAAACGG-3'  (SEQ ID No.11)

5'-CCGCTCGAGGTTAGTGGTGCTAATGAACCC-3' (SEQ ID No.12)

Each primer was modified to have NheI recognition site at its 5' end, and XhoI recognition site at its 3' end.

PCR was done with the Expand HF and by means of the DNA Thermal Cycler. The composition of a reaction solution used in this example was as follows:

TABLE 4

| | |
|---|---|
| H$_2$O | 34 µl |
| 10 × Reaction Buffer: | 5 µl 1x |
| 2.5 mM dNTP, Mix: | 5 µl (250 µM) |
| Primer: | 1 µl 2× (20 µM) |
| Template: | 3 µl |
| Expand HF DNA polymerase mix: | 1 µl (3.5 U/TEST) |
| A total liquid volume: | 50 µl |

The above reaction solution (50 µl) was mixed in a reaction tube (0.2 ml) and set in the DNA Thermal Cycler to be subjected to PCR with the following temperature conditions:

94° C. for 3 minutes, 1 cycle;

94° C. for 1 minute, 50° C. for 2 minutes, 72° C. for 2 minutes, 25 cycles; and

72° C. for 7 minutes, 1 cycle.

An amplified product was identified with 1.0% agarose gel electrophoresis. A DNA fragment was isolated and purified in the gel electrophoresis, ligated with the TA cloning vector pT7Blue T-Vector and cloned into the *E. coli* JM109 strain. A plasmid was prepared from the resulting clone, and the base sequence of the cloned DNA fragment was confirmed. As a result, one cloned plasmid having no error was obtained, and it was digested with NheI and XhoI. A digested DNA fragment was identified with 1.0% agarose gel electrophoresis and collected. The collected DNA fragment was ligated with the pET-21 b(+) digested with Nhe I and Xho I (FIG. 1), and the *E. Coli* BL21-CodonPlus (DE3)-RIL strain was transformed with the resulting vector. The plasmid was obtained from 16 transformant clones and analyzed about the presence of the thus inserted DNA fragment to confirm that 6 clones out of them had it therein.

The above *E. coli* transformant was cultured with shaking for 20 hours at 20° C. in a culture medium (1% tryptone, 0.5% yeast extract, 1% sodium chloride, 50 µg/ml ampicillin, 0.1 mM IPTG) containing a 1/10 volume of the medium used for culture for overnight. The medium a 100 ml of the above YPD medium. The transformants were harvested, disrupted with the ultrasonic disintegrator and subjected to SDS-polyacrylamide gel electrophoresis, which showed the existence of a protein with a molecular weight of 80 kDa (FIG. 2-B).

The measurement of the activity of β-1,3-glucanase was carried out with a reaction time of one hour according to Rachel et al. (Gene 226, 147-154 (1999)) by using laminarin (Sigma Co.) as a substrate. The results are shown in Table 5. The activity of β-1,3-glucanase was found in the above *E. coli* transformant showing that β-1,3-glucanase has been produced by the same transformant, while no activity was detected in *E. coli* transformed by the vector pET-21b(+) alone.

The plasmid pEngL prepared from the above transformant was deposited at the International Patent Organism Depositary of National Institute of Advanced Industrial Science and Technology on Jun. 24, 2004 with an acceptance No. FERM AP-20099.

TABLE 5

| | β-1,3-Glucanase Activity OD 500 |
|---|---|
| Blank (pET-21b(+) alone) | not detectable |
| Exo-β-1,3-glucanase | 0.0298 |
| Endo-β-1,3-glucanase | 0.3840 |

EXAMPLE 5

Purification of the Novel endo-β-1,3-glucanase from *E. coli* Transformant

The *E. coli* transformant expressing the novel endo-β-1,3-glucanase was cultured overnight with shaking in the culture medium as in Example 4, harvested, disrupted with the ultrasonic disintegrator and purified with His MicroSpin Purification Module, and subjected to SDS-polyacrylamide gel electrophoresis, showing its molecular weight of 80 kDa.

EXAMPLE 6

Substrate-Specificity of the Novel endo-β-1,3-glucanase

The substrate specificity was studied by using an enzyme solution purified from the *E. coli* transformed with the recombinant expression vector comprising the novel endo-β-1,3-glucanase gene. Thus, the substrate specificity was measured in a one-hour reaction by the same way as in Example 4 according to Rachel et al. (Gene 226, 147-154 (1999)) by using laminarin, chitosan, cellobiose, gentiobiose (Sigma Co.), dextran, pustulan, β-1,6-glucan, and curdlan (Wako Pure Chemical Industries Ltd.) as a substrate. The results are shown in TABLE 6. Since the activity was found for laminarin and curdlan that have β-1,3 main chain, the *E. coli* transformant has been identified to have a capacity of producing β-1,3-glucanase.

TABLE 6

| Substrate | Main Glucose Binding Form | β-1,3-Glucanase Activity (%) |
|---|---|---|
| laminarin | β-1,3 | 100 |
| curdlan | β-1,3 | 39.0 |
| dextran | β-1,6 | 17.1 |
| gentiobiose | β-1,6 | 23.0 |
| pustulan | β-1,6 | 15.0 |
| β-1,6-glucan | β-1,6 | 13.7 |
| chitosan | β-1,4 | 15.2 |
| cellobiose | β-1,4 | 14.2 |

Specifically, the enzyme activity was determined as follows. The enzyme solution (30 µl) was reacted with a 50 mM sodium acetate solution (pH 5.5) containing the substrate such as laminarin (3 mg/ml) for 30 minutes at 37° C. After deactivation of the enzyme by heating in a boiled water for 5 minutes, a coloring agent of a Glucose detection kit, C-II Test Wako (Wako Pure Chemical Industries Ltd.) was added to the solution and heated for 5 minutes at 37° C., followed by the detection of absorbance at 505 nm.

EXAMPLE 7

Optimum pH

Relative activity was measured in accordance with the above enzyme activity measurement method by using 50 mM sodium acetate solution (pH 2.0-10.0) containing the laminarin (3 mg/ml). The enzyme activity was maximized around at pH 5.0. The results are summarized in TABLE 7.

EXAMPLE 8 pH Stability

Residual activity was measured in accordance with the above enzyme activity measurement method after being kept in 50 mM sodium acetate solution (pH 2.0-10.0) containing the laminarin (3 mg/ml) for one hour at 37° C. The results showed pH stability at a range of pH 5.0-7.0. The results are summarized in TABLE 7.

EXAMPLE 9

Optimum Temperature

Relative activity was measured in accordance with the above enzyme activity measurement method at a temperature range of 20-75° C. The enzyme activity was maximized around at 45° C. The results are summarized in TABLE 7.

EXAMPLE 10

Thermal Stability

Residual activity was measured in accordance with the above enzyme activity measurement method by using 50 mM sodium acetate solution (pH 5.5) containing the laminarin (3 mg/ml) for one hour at a temperature range of 20-75° C. The results demonstrated stability of 90% or more up to 55° C., while its residual activity was reduced to about 75% at a temperature up to at 75° C. and was deactivated at a temperature over 75° C. The results are summarized in TABLE 7.

EXAMPLE 11

Calculation of Enzyme Activity

The activity of the novel endo-β-1,3-glucanase was measured in accordance with the above enzyme activity measurement method, and expressed as "U/mg." "One U" is defined as an amount of the enzyme that will generate 1 μ mole product per one minute. The amount of the enzyme contained in the solution was determined in advance by Bradford method-protein-Assay (BioRad Co.). The enzyme solution (800 μl) was mixed with a staining agent (200 μl), and incubated for 5 minutes at a room temperature, followed by detection of absorbance at 595 nm. A total amount of the protein, a total activity, and specific activity are shown in TABLE 7.

EXAMPLE 12

Analysis of the Rate of Enzyme Reaction

Michaelis constant (Km value) and a maximum rate (Vmax value) in an enzyme reaction of the novel endo-β-1,3-glucanase were measured by using laminarin (Sigma Co.) as a substrate. The measurement was done in accordance with the above enzyme activity measurement method by adding the substrate in a range of 0.1-10 mg/ml and serially detecting the absorbance of the reaction mixture at 505 nm to determine a laminarin-decomposing activity. The Uneweaver-Burk blots were made based on the results to give the Km value of 3.62 mg/ml and the Vmax value of 75.02 μmol/min. The results are summarized in TABLE 7.

TABLE 7

| Properties | |
|---|---|
| Optimum pH | 5.0 |
| pH Stability | 5.0-7.0 |
| Optimum Temperature (° C.) | 45 |
| Thermal Stability (° C.) | ~55 |
| Total Protein (mg) | 7500 |
| Total Activity (U) | 297.0 |
| Specific Activity (U/mg) | 25.25 |
| Vmax (μmol/min) | 75.02 |
| Km (mg/ml) | 3.62 |

EXAMPLE 13

HPLC Analysis of Laminariolicosaccharide Having 13 Saccharides Treated with endo-β-1,3-glucanase PA-laminarioligosaccharide having 13 saccharides (SEIKAGAKU Corp.) was reacted with the novel enzyme having the endo-p-1,3-glucanase activity, and the resulting decomposed products were detected by HPLC. The results are shown in FIG. 3 and FIG. 4. The PA-laminarioligosaccharide was dissolved in 10 mM sodium acetate buffer (pH 5.5) at a final concentration of 200 pmol/ml. Oligoaaccharides from trisaccharide to decasaccharide were detected in an early intermediate product obtained by treatment of the PA-laminarioligosaccharide with 0.1 μg/ml of the enzyme for 1, 3 and 10 minutes. It was confirmed that oligosaccharides from heptasaccharide to decasaccharide constituted major decomposed products (FIG. 3). Fruther, oligosaccharides from disaccharide to nonascasaccharide were detected in an early intermediate product obtained by treatment of the PA-laminarioligosaccharide with 10 μg/ml of the enzyme for 1, 3, 10 and 60 minutes. It was confirmed that pligosaccharides from disaccharide to trisaccharide constituted major decomposed products (FIG. 4). From these results obtained from HPLC, it was confirmed that the above β-1,3-glucanase was an endo-type enzyme.

EXAMPLE 14

Construction of *Aspergillus* Expression Vector

A plasmid (pAPTL) was constructed by replacing a marker gene of argB gene in an expression vector plasmid, pMAR5 (Biosci. Biotech. Biochem., 56:1674-1675, 1992) comprising an amylase promoter of *Aspergillus oryzae* with niaD gene of *Aspergillus oryzae*. Thus, the resulting plasmid is an expression vector comprising the niaD gene as a selective marker, and 7 different restriction sites (EcoPI, ClaI, NheI, NotI, SpeI, SmaI and HindIII) between the promoter and terminator of the amylase gene. If an ORF of a desired gene was inserted at the above restriction sites in the same direction as the promoter, the resulting expression vector would express the desired gene under the regulation of the amylase promoter in *Aspergillus* transformed with said expression vector.

PCR was carried out by using the genomic DNA as a template to give a DNA fragment comprising an ORF of the novel endo-β-1,3-glucanase gene. The following two primers prepared based on the base sequence of said gene were used in the PCR:

5'-CTAGCTAGCATGGCGACAATGGCAAACGG-3' (SEQ ID No.13)

5'-GGACTAGTCTATATATTGTTAGTGGTGCTA-3' (SEQ ID No.14)

Each primer was modified to have NheI recognition site at its 5' end, and SpeI recognition site at its 3' end.

PCR was done by using KOD-Plus-DNA polymerase (TOYOBO) and by means of the DNA Thermal Cycler. The composition of a reaction solution used in this example was as follows:

TABLE 8

| $H_2O$ | 32.75 μl | |
|---|---|---|
| 10 × Reaction Buffer: | 5 μl | 1x |
| 2.5 mM dNTP, Mix: | 5 μl | (250 μM) |
| 25 mM MgSO4 | 3 μl | 1.5 mM |
| Primer: | 1 μl | 2x (20 μM) |
| Template: | 1 μl | 1 μg |
| KOD-Plus-DNA polymerase: | 1.25 μl | (1.25 U) |
| A total liquid volume: | 50 μl | |

The above reaction solution (50 μl) was mixed in a reaction tube (0.2 ml) and set in the DNA Thermal Cycler to be subjected to PCR with the following temperature conditions:

95° C. for 2 minutes, 1 cycle;
95° C. for 0.5 minute, 58° C. for 0.5 minute, 72° C. for 4 minutes, 30 cycles; and
72° C. for 4 minutes, 1 cycle.

An amplified product was digested with NheI and SpeI, and identified with 1.0% agarose gel electrophoresis. A DNA fragment was isolated and purified in the gel electrophoresis, ligated with pAPTL digested with the same restriction enzymes and cloned into the *E. coli* JM109 strain. The plasmid pEGO prepared from the above transformant was deposited at the International Patent Organism Depository of National Institute of Advanced Industrial Science and Technology on Jun. 24, 2004 with an acceptance No. FERM AP-20101.

Production of *Aspergillus* Transformant

An *Aspergillus oryzae* RIB326-15 strain (niaD-deficient strain) was transformed with the above plasmid pEGO by using protoplasts in the presence of PEG in accordance with the calcium chloride method (Mol. Gen. Genet., 218:99-104, 1989). Transformation with 20 μg of pEGO followed by selection of the transformants in CZ medium (DIFCO) gave about 50 colonies. Mono-conidium separation was done for 12 colonies out of the resulting 50 colonies in a minimal medium in order to stabilize their characters. The conidia of these strains were scratched off from an agar plate and inoculated in the YPD medium. After culture with shaking for 24 hours at 30° C., the fungi were collected and their genomic DNA was obtained by using Wizard Genomic DNA Purification Kit (Promega). The resulting genomic DNA was subjected to Southern hybridization to detect whether the desired gene was inserted or not. As a result, it was confirmed that 9 strains had the gene introduced therein, one of which was designated ENG1.

Expression of the Novel endo-β-1,3-glucanase Gene in *Aspergillus oryzae*

The conidia of the ENG1 strain and its parent strain (a wild type for endo-β-1,3-glucanase), *Aspergillus oryzae* RIB326-15 strain, were inoculated in the YPD medium. After culture with shaking for 24 hours at 30° C., the fungi were transferred to an oligotrophic medium supplemented with 1% maltose and cultured with shaking further for 24 hours at 30° C. The fungi were collected, put into a mortar containing liquid nitrogen and crushed with a pestle. An approximately half amount of the crushed fungi was taken into 5 ml of an extraction buffer (50 mM potassium phosphate buffer, pH7.0, 10 mM ethylene diamine trisodium tetraacetate, 0.1% Triton X-100, 0.1% N-lauroylsarcosine sodium, 10 mM 2-mercaptoethanol), stirred sufficiently, subjected to centrifugation for 10 minutes at 10,000 rpm to precipitate insoluble materials, followed by collection of the supernatant of the thus disrupted fungi. The β-1,3-glucanase activity was determined by using said supernatant in accordance with the above enzyme activity measurement methods. The results are shown in TABLE 9.

TABLE 9

| | β-1,3-glucanase activity (u/mg) |
|---|---|
| ENG1 | 1.37 |
| RIB326-15 | 0.69 |

It was observed that the β-1,3-glucanase activity was increased by twice in the ENG1 strain compared to the parent strain, showing that the productivity of β-1,3-glucanase was increased in ENG1 strain. The ENG1 strain was deposited at the International Patent Organism Depository of National Institute of Advanced Industrial Science and Technology on Jun. 24, 2004 with an acceptance No. FERM AP-20098.

INDUSTRIAL APPLICABILITY THE INVENTION

It is expected that a safe and efficient reduction of the molecular weight of β-1,3-glucanase may be done by using the genes or proteins according to the present invention, and that the productivity of water-soluble β-1,3-glucan, an anti-tumor activity of which is now drawing attention, and foods containing it may be increased accordingly.

What is claimed is:

1. An isolated polynucleotide sequence encoding one of the following proteins:
   (a) β-1,3-glucanase obtained from *Aspergillus oryzae* and having a molecular weight of 62 kD, and
   (b) a protein consisting of an amino acid sequence of SEQ ID No:2.

2. An isolated polynucleotide sequence comprising one of the following DNAs:
   (a) a DNA consisting of a nucleotide sequence of SEQ ID No: 1,
   (b) a DNA which hybridizes with a nucleic acid comprising the nucleotide sequence of SEQ ID No:1 or its complete complement thereof under stringent conditions comprising a sodium concentration of 150 mM at a pH of 6-8 and 68° C. and encoding a protein having exo-β-1,3-glucanase activity.

3. An isolated polynucleotide sequence encoding one of the following proteins:
   (a) β-1,3-glucanase obtained from *Aspergillus oryzae* and having a molecular weight of 80 kD, and
   (b) a protein consisting of an amino acid sequence of SEQ ID No:4.

4. An isolated polynucleotide sequence comprising one of the following DNAs:
   (a) a DNA consisting of a nucleotide sequence of SEQ ID No:3, and
   (b) a DNA, which hybridizes with a nucleic acid comprising the nucleotide sequence of SEQ ID No:3 or its complete complement thereof under stringent conditions comprising a sodium concentration of 150 mM at a pH of 6-8 and 68° C. and encoding a protein having endo-β-1,3-glucanase activity.

5. A recombinant expression vector comprising the polynucleotide sequence according to any one of claims 1-4.

6. A microorganism comprising the recombinant expression vector according to claim 5.

7. A method for the production of exo-, or endo-β-1,3-glucanase, comprising culturing the microorganism according to claim 6 in a culture medium, and collecting the exo-, or endo-β-1,3-glucanase from culture material.

* * * * *

UNITED STATES PATENT AND TRADEMARK OFFICE
CERTIFICATE OF CORRECTION

PATENT NO. : 7,285,407 B2
APPLICATION NO. : 11/085185
DATED : October 23, 2007
INVENTOR(S) : Masayuki Machida et al.

It is certified that error appears in the above-identified patent and that said Letters Patent is hereby corrected as shown below:

Title Pg, Item (73) Assignee: insert,

--National Research Institute of Brewing, Hiroshima (JP)--

Signed and Sealed this

Seventeenth Day of August, 2010

David J. Kappos
*Director of the United States Patent and Trademark Office*